United States Patent [19]
Callingham et al.

[11] Patent Number: 4,650,670
[45] Date of Patent: Mar. 17, 1987

[54] SKIN COMPOSITION

[75] Inventors: Martin Callingham; Dwaipayan Chaudhuri, both of London; Kenneth V. Curry, Camberley; Barry G. Pike, Workingham; Michael B. Taylor, Old Headington, all of England

[73] Assignee: Lever Brothers Company, New York, N.Y.

[21] Appl. No.: 159,752

[22] Filed: Jun. 16, 1980

Related U.S. Application Data

[63] Continuation-in-part of Ser. No. 931,269, Aug. 4, 1978, abandoned, which is a continuation of Ser. No. 764,950, Feb. 2, 1977, abandoned, which is a continuation of Ser. No. 557,390, Mar. 11, 1975, abandoned.

[30] Foreign Application Priority Data

Mar. 13, 1974 [GB] United Kingdom ............... 11156/74

[51] Int. Cl.$^4$ ........................... A61K 7/32; A61K 7/38
[52] U.S. Cl. .............................. 424/65; 424/DIG. 5; 424/68; 424/69
[58] Field of Search ........... 424/65, 362, 361, DIG. 5, 424/60

[56] References Cited

U.S. PATENT DOCUMENTS 3,485,915 12/1969 Gerstein et al. .
4,272,514 6/1981 Spence ................................. 424/69

OTHER PUBLICATIONS

Rovesti, "Les Talcs Orthodermiques", Parf. Cosm. Sav., 9, 276, (1966), (translation of relevant portions from pp. 280 and 281).

Primary Examiner—Dale R. Ore
Attorney, Agent, or Firm—Milton L. Honig; James J. Farrell

[57] ABSTRACT

A personal, propellant-free antiperspirant product contains a moisture-absorbent polymer instead of or in addition to the usual metal salt. The product is applied to the skin to give a dry deposit containing the polymer for absorbing skin moisture such as perspiration. The polymer is capable of absorbing an amount of moisture at least equal to its own weight after depositing the product onto the skin.

14 Claims, No Drawings

SKIN COMPOSITION

This application is a continuation-in-part of application Ser. No. 931,269 filed Aug. 4, 1978, now abandoned, which in turn is a continuation of application Ser. No. 764,950, filed Feb. 2, 1977, now abandoned, which in turn is a continuation of application Ser. No. 557,390, filed Mar. 11, 1975, also abandoned.

The invention relates to antiperspirant compositions for application to human skin in solid or liquid form. More particularly the invention relates to solid, liquid or semi-solid propellant-free antiperspirant compositions which are dispensible from suitable applicators; such compositions are based on moisture-absorbent materials which are generally non-astringent in nature and which help to make the composition when deposited on the skin non-staining and milder to the skin.

Antiperspirant compositions generally contain an astringent, such as aluminum chlorhydrate or zinc phenol sulphonate, which is believed to depress the formation of perspiration from sweat glands. These astringents can be applied to the skin in the form of a waxy stick or from a roll-ball applicator.

We have now devised an entirely new type of composition for limiting the manifestation of perspiration on the skin which does not necessarily require the use of astringent perspiration depressants such as those exemplified above and which therefore increases the mildness of the composition by obviating the irritating effect that astringents and their by-products can produce. Where mildness is of less consequence, astringent antiperspirant agents can if desired be incorporated in compositions according to the invention. Therefore, instead of relying entirely on chemical suppression of perspiration at source, we employ a means whereby perspiration can be absorbed at the skin surface as soon as it is formed, thus maintaining the skin in an apparently dry condition. This is achieved by depositing on the skin a composition containing a material having a high capacity for absorbing superficial skin moisture. It follows that transfer of perspiration from the skin to adjacent clothing can also be limited or prevented completely.

Accordingly, the invention provides a propellant-free antiperspirant composition for application to human skin to provide an effective amount of a non-toxic, non-irritant, dry to the touch deposit, the total composition comprising as components from about 10 to about 40% by weight of a non-cellulosic moisture-absorbent organic polymer, from about 1% to about 99% by weight of a cosmetically acceptable carrier for the polymer and from 0 to about 5% by weight of the composition of water, the polymer being characterised by its capacity for absorbing an amount of moisture at least equal to its own weight after deposition of the composition onto the skin.

Compositions according to the invention are propellant-free solids, liquids or semi-solids and should be prepared and packaged in such a manner that they can be deposited on the skin of the user in a convenient manner. A suitable form of packaging for a solid product is a waxy stick contained in a push-up applicator similar to that used for lipstick. For liquids or semi-solid compositions, a roll-ball or pump spray applicator can be used.

Alternative forms of packaging are possible and it is not intended that the invention be limited only to those forms of packaging exemplified herein.

An important property of the antiperspirant composition is that after applying it on the skin, it forms a non-toxic, non-irritant, dry to the touch, moisture absorbent deposit composed essentially of the moisture-absorbent polymer. It is therefore necessary to select the polymer both for its ability to absorb an appreciable amount of water and for its ability to form a dry deposit on the skin.

By "a dry to the touch deposit" we mean a deposit, film or layer which after application to the skin feels dry and is not sticky or tacky to the touch and which does not normally become sticky in use as it absorbs moisture such as perspiration and to which adjacent clothing will not adhere.

The moisture-absorbent organic polymer is a polymer which is organic rather than inorganic in structure and which can be either synthetic or natural in origin and which can itself be soluble or insoluble in water, while possessing the necessary ability to absorb water. Whereas the polymer should be capable, when deposited onto human skin following application of the antiperspirant composition, of absorbing from the dry state an amount of water at least equal to its own weight, the preferred polymers are capable of absorbing a greater proportion of water. For example, some polymers after deposition can absorb up to 5 to 10 times their own weight of moisture or even more and still remain on the skin in a dry to the touch state.

The preferred polymers according to the invention are those which exhibit the greatest capacity for absorbing water, although many of these highly absorbent polymers are costly to produce and hence may be impracticable to use for economic reasons.

Moisture-absorbent polymers for use according to the invention should preferably also have the ability of losing absorbed moisture by evaporation while in contact with the skin, so that they can thereby be self-regenerating to a state of increased moisture absorbency and so prolong their antiperspirant effectiveness.

This property of moisture-absorbancy can readily be assessed by simply adding water to a deposit of the test polymer on a suitable surface to simulate skin until the deposit appears wet and hence is no longer dry to the touch. The moisture uptake, and also the ability subsequently to lose absorbed moisture by evaporation, can then be assessed gravimetrically.

Moisture-absorbent polymers which we have found to be particularly suitable include certain non-cellulosic polysaccharides, polypeptides, vinyl carboxy polymers and copolymers and mixtures thereof. Examples of the preferred polymers can conveniently be classified as follows:

a. Water soluble polymers
   i. Of natural origin: sodium alginate, potassium alginate, guar gum, locust bean gum, low methoxy pectins, agar, furcellaran, xanthan gum, gelatin.
   ii. Of synthetic origin: polyethylene oxides (as described by Glicksman in "Gum Technology in the Food Industry" (1969) at pages 495–505), polyvinylpyrrolidone (see Glicksman, ibid at pages 473–483), copolymers of methyl vinyl ether and maleic anhydrides (as sold under the tradename GANTREZ by the GAF Corporation), linear ionenes (see Rembaum et al, J. Polymer Science (Polymer Letter), 6, 159–171 (1968)).

b. Water insoluble polymers
   i. Of natural origin: mixed salts of calcium and sodium alginate, crosslinked, dextrans, calcium alginate, alginic acid, pregelatinised starches (see Glicksman, ibid at pages 300–301), chemically modified starches (see Glicksman, ibid at pages 310–316), and especially those identified and prepared by the methods set out in U.S. Pat. No. 3002823; and starch copolymers such as hydrolysed (particularly base-hydrolysed) starch—polyacrylonitrile graft copolymers—especially those graft copolymers identified and prepared by the methods set out in Journal of Applied Polymer Science, Volume 13, pages 2007–2017 (1969), and Volume 15, pages 3015–3024.

ii. Of synthetic origin: crosslinked polyacrylamides (see Leonard in "Vinyl and Diene Monomers" Pt I at pages 98–99), crosslinked polyacrylic acids (see Glicksman, ibid at pages 483–484), crosslinked polyhydroxyethyl methacrylate (see Simpson in "Bio-Medical Engineering" 4, (February 1969) at pages 65–68), crosslinked polyvinyl alcohol (see Warson in "Polyvinyl Alcohols and Copolymers" University of Bradford Symposium, 1967), crosslinked polyvinylpyrrolidone (see Glicksman, ibid at pages 473–483), sulphonated polystyrene crosslinked with di-vinyl benzene, quaternised polyvinyl pyridine crosslinked with di-vinyl benzene, crosslinked or branched ionenes (see Reinbaum et al. in J. Polymer Science (Polymer Letters), I (1969) at pages 295–402).

The proportion of the polymer in the antiperspirant composition according to the invention will generally depend on the physical nature of the composition and on the proportions of the other ingredients, particularly the carrier, which are also present.

Generally it can be stated that the proportion of the polymer or mixtures of polymers in the composition is from about 10 to about 40%, preferably from about 15 to 25% by weight of the composition.

It is also necessary to incorporate in the antiperspirant composition according to the invention, a cosmetically acceptable carrier which can function in a variety of ways in improving the effectiveness of the composition. In particular, the presence of a carrier can improve initial adhesion of the moisture-absorbent polymer to the skin, thus aiding in its retention by the skin as it is applied. Also, a carrier can function as a diluent, lubricant or as a spreading agent to facilitate uniform distribution of the moisture-absorbent polymer on the skin.

In the case where the antiperspirant composition is in the form of a liquid or semi-solid in which the polymer is suspended or dissolved, a carrier such as isopropyl myristate, hexylene glycol, dipropylene glycol, ethanol or other alcohols such as poly-lower alkoxylated cetyl alcohols, or esters such as di-n-butylphthalate, diethyl sebacate, di-isopropyl adipate and o-ethyl, ethyl-carboxymethyl phthalate and mixtures thereof, is particularly effective in improving the adherance of the moisture-absorbent polymer to the skin.

When the antiperspirant composition is a solid such as a dry powder, a powder carrier such as talc, chalk or starch can optionally be included in the composition as a diluent and lubricant to promote uniform distribution on the skin of the moisture-absorbent polymer.

When the antiperspirant composition is a solid such as a waxy stick, a carrier such as stearic acid and glycerine can be employed.

The amount of carrier in the antiperspirant composition can form from about 1% to about 99% by weight of the composition. The preferred level of carrier is from about 1% to about 50%, most preferably from about 5% to about 20% by weight of the composition.

The composition can comprise up to about 5% by weight of water. If more than about 5% by weight of water is present, then the composition on application to the skin is likely to be too wet to function effectively as an antiperspirant.

In addition to the ingredients of the composition as set out hereinbefore, minor ingredients can optionally also be included. As an example, germicides can be incorporated in the antiperspirant composition. Suitable germicides, by way of example only, are trichlorocarbanilide, trifluoromethylcarbanilide, tribromosalicylanilide and 2,4,4'trichloro-2-hydroxydiphenyl ether.

Such germicides when used can be employed in an amount of up to about 0.5% by weight of the composition in order to inhibit the proliferation of skin bacteria and reduce or prevent the development of unpleasant odors.

It is also possible optionally to include odor suppressors (such as those disclosed in Dutch Patent Application No. 7409704) in the antiperspirant composition, usually at a concentration in the composition of up to about 20% by weight.

As we have stated, it is also possible to incorporate as a further optional ingredient, an effective amount of a perspiration depressant such as, for example, aluminum chlorhydrate, aluminum chloroalcoholates, zinc phenol sulphonate, zirconium halide hydrates and tetraphenyl boron.

Such antiperspirant agents when used can be employed in an amount of up to about 30% by weight of the composition. Usually, when present, these agents form from 10 to 20% by weight of the composition.

It is also possible to include in antiperspirant compositions according to the invention anticholinergic agents such as trimethylacetyl scopalamine hydrochloride.

It may be necessary to include thickeners such as hydroxypropylcellulose or sodium stearate, or suspending agents such as pyrogenic silicas or montmorillonite clays, in the antiperspirant composition. Furthermore, perfumes and coloring matter can be added.

The composition of the invention is free from propellants, such as for example, the conventional fluorohydrocarbon, hydrocarbon and natural gas propellants, since the applicators from which the compositions are dispensed are other than those which function with the aid of such propellants.

The invention also provides a method for eliminating perspiration from the human skin by applying thereto an effective amount of the composition defined hereinbefore. In order to function as an antiperspirant, the composition is applied to the skin, for example the armpit of the user, so as to provide a moisture absorbent deposit on the skin. The moisture absorbent polymer then functions to absorb moisture as it is secreted from the skin in the form of perspiration so that adjacent clothing is protected, at least for a limited time, from contact with perspiration. This period of protection will depend on the capacity of the polymer to absorb moisture and its loading on the skin, as well as the rate at which the user produces perspiration. Clearly it is, as we have stated, an advantage if the polymer can lose moisture by evaporation while on the skin, so that its effectiveness as an antiperspirant can be prolonged.

The invention is illustrated by the following Examples.

EXAMPLE 1

This Example illustrates the formulation of an antiperspirant composition for use in a roll-ball applicator. The following ingredients were mixed together.

|  | % by weight |
| --- | --- |
| Calcium sodium alginate | 25.0 |
| Hydroxypropyl cellulose | 0.6 |
| Pyrogenic silica | 3.0 |
| 2-ethyl-1,3-hexanediol | 5.0 |
| Perfume | q.s. |
| Industrial Methylated Spirit | to 100 |

The liquid product so produced can be dispensed from a roll-ball applicator to give, when dry, a smooth film on the skin consisting mainly of calcium sodium alginate, which had good perspiration absorbing properties and which functioned well as a body malodor suppressor.

EXAMPLE 2

This Example illustrates the formulation of a solid antiperspirant composition for use in a stick applicator. The following ingredients were mixed together.

|  | % by weight |
| --- | --- |
| Calcium sodium alginate | 17.0 |
| Stearic acid | 4.6 |
| Sodium hydroxide | 0.7 |
| Glycerine | 2.5 |
| Ethylene glycol monoethyl ether | 2.5 |
| Water | 4.2 |
| Industrial Methylated Spirit | 68.5 |

The solid product so produced was molded into a cylindrical form for use in a stick applicator. This stick product can be used to transfer to the skin a smooth film consisting mainly of calcium sodium alginate after the solvent has evaporated. Good perspiration absorbing properties were reported by users of this product.

EXAMPLE 3

The following formulations are suitable for use as antiperspirant lotions which can, for example, be dispensed from a roll-ball applicator.

| Formulation A | % w/w |
| --- | --- |
| Aluminum chlorhydrate | 10.0 |
| Cross-linked polyvinyl alcohol | 10.0 |
| Calcium sodium alginate | 10.0 |
| Glycerol | 2.0 |
| Pyrogenic silica | 0.5 |
| Hydroxypropyl cellulose | 0.5 |
| Alcohol | to 100 |

| Formulation B | % w/w |
| --- | --- |
| Carragheenate | 5.0 |
| Polyvinyl alcohol | 5.0 |
| Cross-linked polyvinyl alcohol | 5.0 |
| Calcium sodium alginate | 5.0 |
| Glycerol | 1.0 |
| Isopropyl myristate | 1.0 |
| Pyrogenic silica | 0.7 |
| Hydroxypropyl cellulose | 0.5 |
| Alcohol | to 100 |

What is claimed is:

1. A propellant-free dry powder composition adapted for application to the human skin to provide an effective amount of a non-toxic, non-irritant, dry to the touch deposit, comprising a mixture of a moisture-absorbent graft copolymer and a powder carrier, said copolymer being a hydrolyzed starch-polyacrylonitrile graft polymer having a capacity for absorbing an amount of moisture at least 5 to 10 times or more its own weight after deposition of the composition onto the skin, said carrier being a conventional body powder, such as talc, chalk or starch, said copolymer being present in an amount effective to absorb an appreciable amount of water to form a dry deposition on the skin and said carrier for the copolymer being present in an amount of up to about 99% by weight of said composition.

2. The composition as defined in claim 1, wherein the graft polymer is base hydrolyzed.

3. The composition according to claim 1 wherein the powder carrier is talc, chalk or starch.

4. The composition as defined in claim 1, wherein the graft polymer is present in an amount from about 15 to 25% by weight.

5. The composition as defined in claim 1, wherein the graft polymer and powder carrier are present in amounts of about 10% and 50% by weight, respectively.

6. The composition as defined in claim 1, wherein the powder carrier is talc.

7. The composition according to claim 6 wherein the graft polymer and talc are present in amounts of about 10% and 50% by weight, respectively.

8. The composition according to claim 6 wherein the graft polymer is present in an amount of about 10% by weight of the composition.

9. The composition according to claim 6 wherein the graft polymer is present in an amount of about 25% by weight of the composition.

10. A propellant-free antiperspirant composition for application to the human skin to provide an effective amount of a non-toxic, non-irritant, dry to the touch deposit, the composition comprising as components from about 10 to about 40% by weight of a non-cellulosic moisture-absorbent water-soluble polymer of natural origin selected from the group consisting of sodium alginate, potassium alginate, guar gum, locust bean gum, low methoxy pectins, agar, furcellaran, xanthan gum, gelatin and mixtures thereof, from about 1% to about 99% by weight of a cosmetically acceptable carrier for the polymer, and from 0 to about 5% by weight of the composition of water, the polymer being characterized by its capacity for absorbing an amount of moisture at least equal to 10 times its own weight after deposition of the composition onto the skin.

11. A propellant-free antiperspirant composition for application to the human skin to provide an effective amount of a non-toxic, non-irritant, dry to the touch deposit, the composition comprising as components from about 10 to about 40% by weight of a non-cellulosic moisture-absorbent, water-insoluble polymer of natural origin selected from the group consisting of mixed salts of calcium and sodium alginate, crosslinked dextrans, calcium alginate, alginic acid, pregelatinised starches, chemically modified starches, hydrolysed starch-polyacrylonitrile graft copolymers and mixtures thereof, from about 1% to about 99% by weight of a cosmetically acceptable carrier for the polymer, and from 0 to about 5% by weight of the composition of water, the polymer being characterized by its capacity for absorbing an amount of moisture at least equal to 10 times its own weight after deposition of the composition onto the skin.

12. A propellant-free antiperspirant composition for application to the human skin to provide an effective amount of a non-toxic, non-irritant, dry to the touch deposit, the composition comprising from about 10 to about 40% by weight of a cross-linked polyacrylic acid, and from 0 to about 5% by weight of the composition of water, the cross-linked polyacrylic acid being characterized by its capacity for absorbing an amount of moisture at least equal to ten times its own weight after deposition of the composition onto the skin.

13. A propellant-free antiperspirant composition for application to the human skin to provide an effective amount of a non-toxic, non-irritant, dry to the touch deposit, the composition comprising as components from about 10 to about 40% by weight of a chemically modified starch, from about 1% to about 99% by weight of a cosmetically acceptable carrier for the chemically modified starch, and from 0 to about 5% by weight of the composition of water, the chemically modified starch being characterized by its capacity for absorbing an amount of moisture at least equal to 10 times its own weight after deposition of the composition onto the skin.

14. A propellant-free antiperspirant composition for application to the human skin to provide an effective amount of a non-toxic, non-irritant, dry to the touch deposit, the composition comprising as components from about 10 to about 40% by weight of a hydrolyzed starch-polyacrylonitrile graft copolymer, from about 1% to about 99% by weight of a cosmetically acceptable carrier for the hydrolyzed starch-polyacrylonitrile graft copolymer, and from 0 to about 5% by weight of the composition of water, the hydrolyzed starch-polyacrylonitrile graft copolymer being characterized by its capacity for absorbing an amount of water at least equal to 10 times its own weight after deposition of the composition onto the skin.

* * * * *